United States Patent [19]

Samuels et al.

[11] 4,108,161
[45] * Aug. 22, 1978

[54] GRAFT FORMING DEVICE

[76] Inventors: Peter B. Samuels, 14708 Sutton St., Sherman Oaks, Calif. 91403; Ernest C. Wood, 2461 Ivanhoe Dr., Los Angeles, Calif. 90039

[*] Notice: The portion of the term of this patent subsequent to Dec. 6, 1994, has been disclaimed.

[21] Appl. No.: 739,650

[22] Filed: Nov. 8, 1976

Related U.S. Application Data

[63] Continuation-in-part of Ser. No. 626,070, Oct. 28, 1975.
[51] Int. Cl.² .......................................... A61B 19/02
[52] U.S. Cl. ...................................... 128/1 R; 3/1.4; 128/334 R; 206/363; 206/438
[58] Field of Search ................ 128/1 R, 334 R; 3/1, 3/1.4; 260/363, 364, 438

[56] References Cited
U.S. PATENT DOCUMENTS 3,154,080  10/1964  Rowan et al. .................. 128/349 R
3,625,198  12/1971  Sparks ............................. 128/1 R
3,916,874  11/1975  Perrin ............................. 128/1 R
4,011,947   3/1977  Sawyer ........................... 206/363
4,061,134  12/1977  Samuels et al. ................ 128/

OTHER PUBLICATIONS

USCL pamphlet, Mar. 1973 — "Sauvage External Dacron Velour Prosthesis".

Primary Examiner—Dalton L. Truluck
Attorney, Agent, or Firm—McDougall, Hersh & Scott

[57] ABSTRACT

A device for the preparation of a graft in which a flexible tubular porous base member is suspended within a tubular enclosure with means for sealing the enclosure and for the introduction of blood while removing air from the enclosure co-incident with the introduction of blood and in which the porous tubular base member onto which the blood is clotted in forming the graft embodies axially spaced corrugations to permit stretchability for working the graft to enhance permeation of the blood and to permit easy bending without collapse.

10 Claims, 5 Drawing Figures

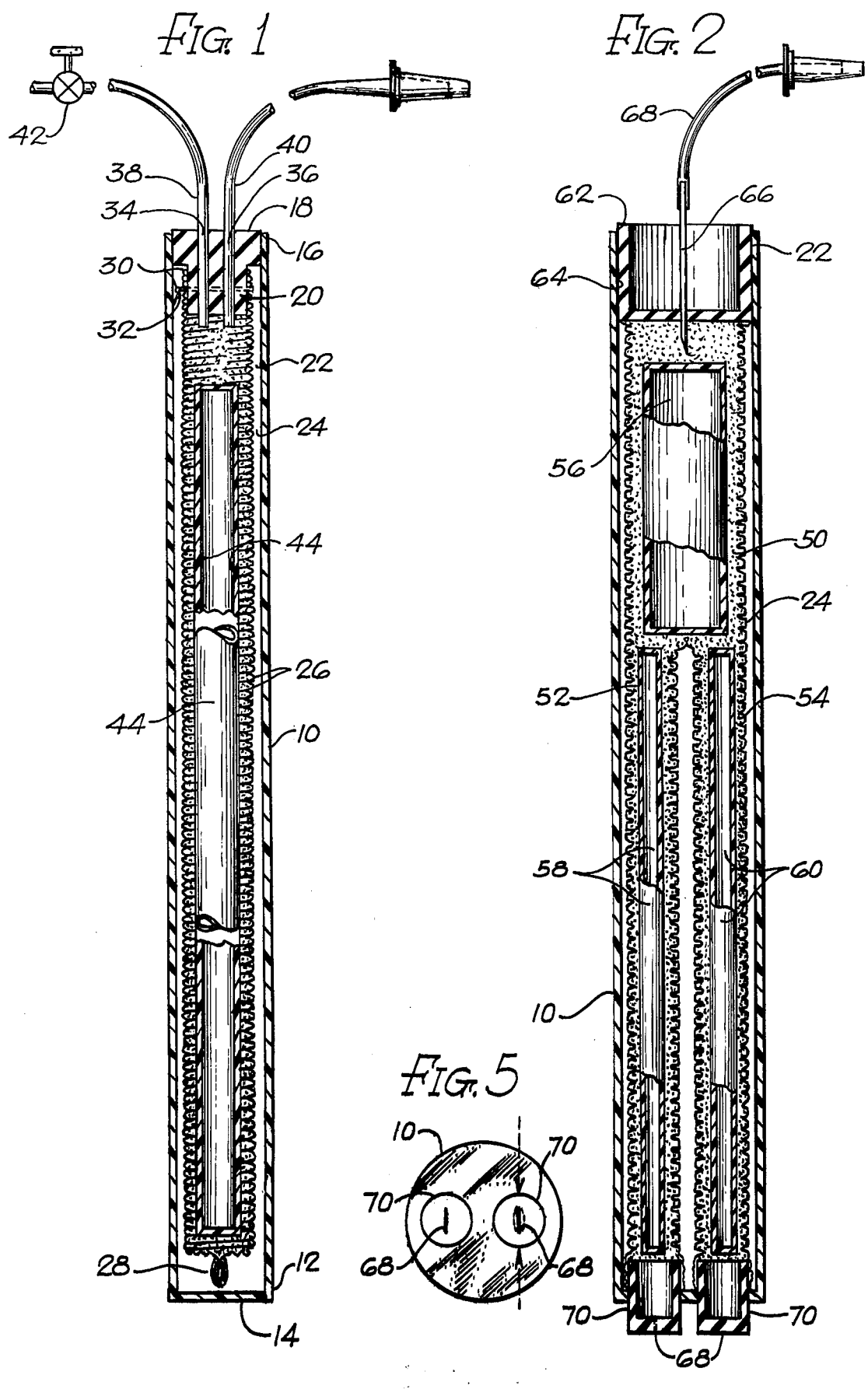

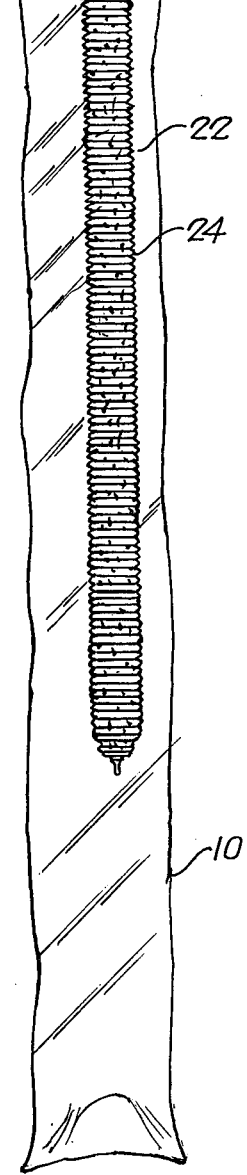
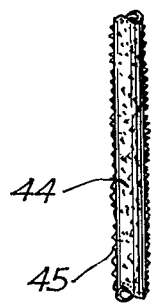
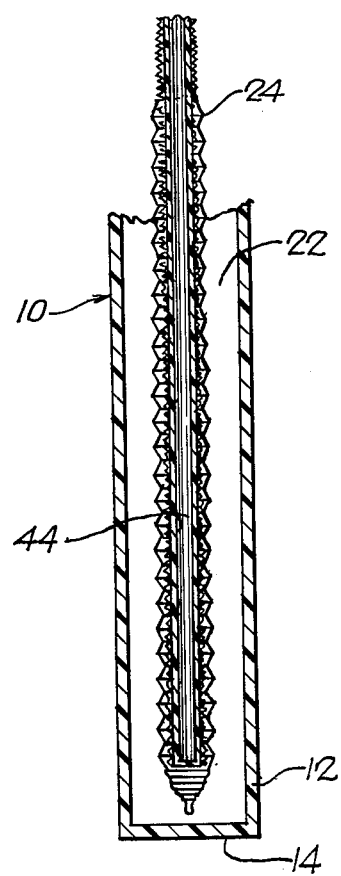
FIG. 3
FIG. 4

GRAFT FORMING DEVICE

This is a continuation-in-part of our copending application Ser. No. 626,070, filed Oct. 28, 1975, and entitled "Arterial Graft Device and Method for Preparing Same."

In the aforementioned copending application, description is made of grafts in the form of corrugated, elongate porous base members suspended within a rigid or flexible enclosure. The graft is prepared by the introduction of patient's blood into the interior of the enclosure for clotting onto the walls of the base member while the sealed relationship is maintained so as to enable blood clotting to be effected under aseptic conditions. The prepared graft can be retained in the sealed enclosure to prevent contamination until immediately prior to removal for use.

A number of problems have been encountered which interfere with the efficient utilization of the device. For example, the pressure buildup, which occurs within the enclosure during the introduction of patient's blood, sometimes interferes with the smooth flow into the enclosure when the blood is removed directly from an arterial vein or storage vessel.

Thus it is an object of this invention to produce a device of the type described which provides for enhanced utilization in the preparation of an arterial graft.

These and other objects and advantages of this invention will hereinafter appear, and for purposes of illustration but not of limitation, embodiments of the invention are shown in the accompanying drawings in which —

FIG. 1 is an elevational view partially in section of a device embodying the features of this invention;

FIG. 2 is a sectional elevational view showing a modification in the device;

FIG. 3 is an elevational view showing a still further modification;

FIG. 4 is a fragmentary view of a further modification; and

FIG. 5 is a view showing the ends of the split plugs in FIG. 2.

In the modification shown in FIG. 1, the enclosure is in the form of an elongate tubular member 10 formed of a rigid, fluid and vapor impervious material, such as glass or plastic, preferably either transparent or translucent so as to be able to see through and observe the elements contained therein. For this purpose, the tubular member 10 may be formed by extrusion of such plastic materials as a polyacrylate or polyalkyl acrylate, such as polymethylmethacrylate, polybutylmethacrylate, and the like, polystyrene, polytetrafluoromethylene (Teflon), polyamide (nylon), polyethylene, polypropylene, or ethylene propylene copolymer, acrylic copolymers with styrene and/or butadiene, cellulose ethers or esters, such as cellulose acetate, and the like, or of glass.

One end 12 of the tubular member 10 is closed as by means of a stopper or plug 14, or by heat fusion of the plastic material. The other open end 16 is provided with a removable stopper 18 adapted to be inserted into the open end of the tubular member for sealing engagement with the adjacent walls thereof. An extension 20 of smaller cross-section depends from the bottom side of the stopper into the interior of the tubular member to provide an annular space between the inner walls of the tubular member and the extension.

Suspended within the chamber 22 of the tubular member 10 is an elongate pervious member 24 which forms the base of the arterial graft. The member 24 can be woven of a textile material, using natural or synthetic fibers, such as Mylar, dacron, rayon and the like, or it can be fabricated of a plastic material, such as cellulose acetate, cellulose butyrate and the like. The porous base member 24 is in the form of an elongate tubular member dimensioned to have a length slightly less than the length of the enclosed chamber 22 and a diameter which is less than the internal diameter of the chamber 22 so as to provide for free annular space therebetween. The tubular member 24 is preferably formed with corrugations 26 substantially throughout its length to provide stretchability in the axial direction and bendability in every direction while preventing collapse. The corrugations 26, which are preferably in the form of axially spaced circumferential ribs formed in the walls of the tubular member 24, enable the base member to be stretched in a manner to open the interstices of the porous fabric to enable better penetration and more complete occlusion of the interstices during clotting of the blood.

In the illustrated modification, one end of the porous base member 24 is closed, as by stitching, or by clips 28 while the other open end 30 is secured to the stopper 18 for suspension from the stopper into the interior of the chamber 22. In the illustrated modification of FIG. 1, the open end 30 of the base member is telescoped about the extension 20 to which it is releasably secured by means of a tie wire, cord, resilient band 32 or the like which wraps about the portion of the porous base member encircling the extension 22.

The stopper 18 is formed with a pair of passages 34 and 36 to enable insertion of a pair of tubular members 38 and 40, respectively, through the stopper and into the chamber for communication therewith. One tubular member 38 is adapted to communicate with the source of blood, such as an artery, vein or blood bank for the introduction of blood into the chamber and preferably into the interior of the porous base member 24. The tubular member can be provided with a valve 42 for flow control and for sealing off the tubular member for periods of time other than when blood or other fluid is being introduced into the chamber. The other tubular member 40 functions as a vent for the release of gas displaced from the chamber as blood or other fluid is introduced therein. Instead, the tubular member 40 may be connected to a source for inducing a vacuum within the chamber, such as an aspirator or vacuum pump, whereby the blood or other fluid is drawn through the other tubular member 42 into the chamber.

Considerable advantage is derived from the use of a filler member 44 adapted to occupy a volume within the chamber, and preferably within the porous base member 24, thereby to minimize the amount of blood required to be introduced to vent the chamber for wetting out the base member throughout its length. For this purpose, as illustrated in the drawing, use is made of a hollow tube 44 dimensioned to have a length slightly less than the length of the porous base member 24 and a cross-section which is less than the interior cross-section of the base member to enable the hollow tube to be disposed within the porous base member to occupy the major portion of the volume thereof. The filler tube can be in the form of a hollow member formed of a material which is not reactive with the blood, such as glass or plastic, or it can be in the form of a solid rod of glass, plastic or other impervious material.

When the necessary amount of patient's blood or other fluid has been introduced into the chamber 22 the tubular member 42 and the vent 40 are closed, as by valve means, to re-seal the chamber. Thereafter the tubular member is rocked or otherwise agitated to cause distribution of the blood for complete and uniform permeation of the base member and clotting to form a lining in the form of a coating which permeates the interstices of the porous base member.

When completely permeated, the formed graft sealed within the chamber 22 can be set aside until immediately prior to use of the prepared graft. At such time, the stopper 18 can be removed to enable removal of the prepared graft for use as an arterial graft or the like.

It will be apparent from the description that the preparation of the graft is achieved under aseptic conditions in that the blood and the elements making up the graft are processed without exposure to atmospheric conditions and without being touched by another during preparation of the graft.

By way of modification to enhance the characteristics of the graft and its preparation, the porous base member 24 can be coated with a non-wettable substance, such as a liquid silicone or wax. By way of still further modification, the base member 24 can be cleaned for coating the surfaces with an antibiotic for the purpose of minimizing undesirable enzymatic reactions and to destroy undesirable microorganisms which might be present in the blood clotted onto the base member during formation of the graft.

The base member can be pretreated with an anticoagulant to prevent undesirable coagulation of the blood before complete permeation of the base member has been achieved.

In the modification shown in FIG. 2, the base member 24 is formed of a trunk portion 50 of larger cross-section which subdivides into a pair of branches 52 and 54 of smaller cross-section, but as continuations from the trunk. As in the previous modification, the interior of the trunk portion 50 is occupied by a filler rod 56 while the branched portions 52 and 54 are each partially filled by rods 58 and 60, respectively, of smaller cross-section.

Instead of making use of a sealing plug having an extension onto which the open end of the trunk 50 is tied, in the modification shown in FIG. 2, the open end of the chamber 22 is sealed with a cup-shaped stopper 62 with the open upper end portion 64 of the porous base member between the stopper and the adjacent wall of the tubular member releasably to secure the porous base member in position of use within the chamber.

Instead of making use of tubular members insertable through passages in the closure for communication with the interior of the chamber, the stopper 62 is adapted to be pierced by a hollow needle 66 for communicating the interior of the chamber with a tubular member 68 adapted to be connected to an artery, vein or other source of patient's blood for introduction into the chamber. A suitable valve (not shown) can be provided for sealing the tubular member or, in the preferred arrangement, the stopper 62 is formed of a rubber-like or elastic material which becomes re-sealed upon removal of the hollow needle 66.

Instead of making use of a tubular member insertable for removal of gases from within the chamber, as illustrated in the modification shown in FIG. 1, sealable passages communicating with the interior of the chamber for venting gases are provided in the form of elongate slits 68 in sealing plugs 70 formed of resilient or rubber-like plastic material and insertable into the opposite open ends of the chamber. The plugs 70 are of the type wherein the slits 68 are open when the plug is deformed by pressure applied in the direction crosswise of the slits and which automatically close to provide a sealing relation when the pressure is released to enable the plug to return to its relaxed state.

As in the previous modification, the chamber is filled with patient's blood by inserting the hollow needle 66 through the stopper 62 and communicating the needle with an artery or other source of blood. To enable smooth flow into the chamber, the buildup of pressure is avoided by venting air or gases from within the chamber by compressing the plugs to open the slit valve. When blood in sufficient amount has been introduced into the chamber, clotting to coat the walls of the porous base member is effected as described and the assembly set aside for subsequent use.

In the modification shown in FIG. 3, the porous base member 24 is housed within a chamber 22 formed of a flexible, impervious plastic material which enables the elements to be worked after the blood has been introduced to enhance the clotting of the blood and for working the blood through the porous base member.

The enclosure, in the form of a stocking, is fabricated of a transparent, impervious plastic material which is highly flexible to enable the assembly to be worked.

The open end of the enclosure is sealed, as in the modification shown in FIG. 1, with a pair of passages 72 and 74 through the stopper 76 to enable insertion of tubular members 78 and 80, respectively, one for the introduction of blood into the interior of the porous base member 24 while the other is adapted to vent the interior of the chamber or for the withdrawal of air to generate a vacuum within the chamber for drawing blood into the chamber from an arterial source.

In the modification, after the patient's blood has been introduced, the stocking is worked uniformly to distribute the blood for coating the walls of the porous base member. Thereafter the unit can be set aside until it is desired to make use of the prepared graft.

In the modification wherein use is made of a flexible enclosure, the filler member is omitted unless use is made of a flexible rod which will enable the unit to be massaged for clotting after instillation of blood.

When, as illustrated in the modification shown in FIGS. 1, 2 or 3, use is made of a filler member in the form of an insert, it is preferred to make use of an insert 44 which is dimensioned to have a length greater than the length of the porous base member 24 so as to stretch the porous base member to enhance permeation of the interstices of the graft when the blood is instilled, as illustrated in FIG. 4. The insert may be coated with a velour-like cloth or terry cloth 45 which serve to clean out the graft during removal of the insert and to aid the formation of clots in the interstices of the porous base material by adding a thrombogenic surface lying just within the graft.

The devices described provide a one step procedure for pre-clotting in which a needle is inserted into the aorta or other exposed artery for allowing the blood to flow into the porous base member while the air is allowed to flow out of the chamber through the vent. The needle is withdrawn and the tubes are capped after which the graft with the blood is set aside and shaken occasionally or massaged in the case of the soft graft. The graft may be removed when it is necessary for placement in the arterial tree and can be tested directly by flushing blood after it has been sewn in place or it can be tested with Heparinized blood under direct vision by reprofusing the graft or a perfusion solution, such as dextran and glucose or Ringer's Lactate with Reparin can be used to test the graft for permeability.

In the preferred modification, the tubes can be incorporated in such manner that the blood is interfused in the inner aspect of the graft and percolates through to the outer aspects of the graft. This results in a very light weight structure which is completely hollow and leaves only a narrow chamber for the percolating blood in which a change in resistance or the absence of blood percolating through the graft on repeated interfusions of blood will provide indication that the graft is clotted.

A further advantage is the ability to detect the presence of clotting in the interstices of the graft as a result of increased resistance on a further attempt to interfuse blood or saline through the chamber.

It will be understood that changes may be made in the details of construction, arrangement and operation without departing from the spirit of the invention, especially as defined in the following claims.

We claim:

1. A device for use in the preparation of a graft for blood vessels comprising a hollow tubular member formed of a fluid impervious material and open at one end, a removable closure adapted to engage the open end of the tubular member in sealing relation, an elongate flexible porous base member suspended from the closure into the hollow tubular member, said porous base member being dimensioned in the crosswise direction to be less than that of the hollow tubular member to provide a spaced relation between the porous base member and the inner wall of the tubular member, said porous base member having axially spaced corrugations to enable the base member to be stretched in the axial direction and bendable in all of the directions without collapse, a passage through said removable closure for insertion of a member connecting the interior of the hollow tubular member with a source of blood, and another sealable passage communicating with the interior of the hollow tubular member for the removal of gases from within the tubular member co-incident with the introduction of blood therein.

2. A device as claimed in claim 1 in which the other sealable passage is in the form of a vent which embodies a valve member controlling the opening and closing of the vent.

3. A device as claimed in claim 1 in which the other passage is in the form of a second passage through the closure for communicating with the interior of the hollow tubular member.

4. A device as claimed in claim 1 in which the hollow tubular member is formed of a translucent plastic material.

5. A device as claimed in claim 1 in which the porous tubular base member is formed of a textile material.

6. A device as claimed in claim 1 in which the porous tubular base member is formed of a plastic material having porous walls.

7. A device as claimed in claim 1 which includes an insert within an elongate flexible porous base member dimensioned to fill the major portion of the interior thereof.

8. A device as claimed in claim 7 in which the insert is dimensioned to have a length greater than the length of the porous tubular base member when in the relaxed state thereby to maintain the tubular base member in a stretched condition.

9. A device as claimed in claim 7 in which the insert is in the form of a hollow rod.

10. A device as claimed in claim 7 in which the insert is in the form of a solid rod.

* * * * *